(12) United States Patent
Chang et al.

(10) Patent No.: US 8,267,914 B1
(45) Date of Patent: Sep. 18, 2012

(54) METHOD AND APPARATUS FOR AC ELECTROSPRAY

(75) Inventors: Hsueh-Chia Chang, Notre Dame, IN (US); Shau-Chun (Paul) Wang, Notre Dame, IN (US); Dmitri Lastochkin, Notre Dame, IN (US); Leslie Yeo, Notre Dame, IN (US); Zachary Gagnon, Notre Dame, IN (US); Siddharth Maheshwari, Notre Dame, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 2355 days.

(21) Appl. No.: 10/965,834

(22) Filed: Oct. 18, 2004

Related U.S. Application Data (60) Provisional application No. 60/511,365, filed on Oct. 16, 2003.

(51) Int. Cl.
*A61M 31/00* (2006.01)
(52) U.S. Cl. ...... 604/500; 604/20; 604/173; 128/200.14
(58) Field of Classification Search ............ 604/46, 604/65, 67, 68, 890.1, 892.1, 20, 173, 500; 128/200.14, 200.16; 222/645
See application file for complete search history.

(56) References Cited

U.S. PATENT DOCUMENTS

| | | | |
|---|---|---|---|
| 6,256,533 B1 * | 7/2001 | Yuzhakov et al. | 604/21 |
| 6,743,211 B1 * | 6/2004 | Prausnitz et al. | 604/239 |
| 2001/0010338 A1 * | 8/2001 | Ganan-Calvo | 239/8 |
| 2002/0099356 A1 * | 7/2002 | Unger et al. | 604/501 |
| 2002/0198512 A1 * | 12/2002 | Seward | 604/522 |
| 2003/0118528 A1 * | 6/2003 | Walters et al. | 424/59 |

OTHER PUBLICATIONS

Ajdari, Armand, "Electro-Osmosis on Inhomogeneously Charged Sufraces" The American Physical Society, 75(4) (Jul. 1995) p. 755-759.
Ajdari, Armand, "Pumping liquids using asymmetric electrode arrays" The American Physical Society, 61(1) (Jan. 2000) p. R45-R48.
Ajdari, Armand, "Transverse Electrokinetic and Microfluidic Effects in Micropatterned Channels: Lubrication Analysis for Slab Geometrics" The American Physical Society, 65 (2001) p. 65 016301-1-65 016301-9.
Asmolov, Evgeny, "The Inertial Lift on a Small Particle in a Weak-Shear Parabolic Flow" Physics of Fluids, 14(1) (Jan. 2002) p. 15-28.

(Continued)

*Primary Examiner* — Kevin C Sirmons
*Assistant Examiner* — Emily Schmidt
(74) *Attorney, Agent, or Firm* — Keith R. Jarosik (57) ABSTRACT

The present invention provides an electrospray device using a high frequency alternating current (AC) above 10 kHz to generate fine micron sized drops. The apparatus generally functions by applying a high frequency alternating current electric field across one or more micro-needles and one or more conducting elements. The present invention may be used to generate aerosol drops for respiratory drug delivery or as a microencapsulation technique for the encapsulation of drugs, DNA, protein, osteogenic or dermatological growth factors, bacteria, viruses, immobilized enzyme receptors and fluorescent particles for controlled release drug delivery, tissue or bone engineering, clinical or environmental field testing and as biosensors for clinical or drug monitoring. In addition, the present invention may be used to synthesize biodegradable fibers as bioscaffolds for tissue engineering, surgical sutures or medical gauze that enhance blood coagulation, and further may be encapsulated by other agents.

41 Claims, 9 Drawing Sheets

OTHER PUBLICATIONS

Barcilon, et al., "Qualitative Properties of Steady-State Poisson-Nernst-Planck Systems: Perturbation and Simulation Study" Journal of Applied Math, 57(3) (Jun. 1997) p. 631-648.
Bazant, et al., "Current-Voltage Relations for Electrochemical Thin Films".
Bazant, et al., "Diffuse-Charge Dynamics in Electrochemical Systems".
Bazant, et al., "Induced-Charge Electrokinetic Phenomena: Theory and Microfluidic Applications" Physical Review Letters 92(6) (Feb. 2004) p. 066101-1-066101-4).
Ben, et al., Linear Particle Assembly and Erasure by AC Electroosmotic Flow: Effects of Faradaic and Capacitive Charging.
Bonnefont, et al., "Asymptotic Analysis of Diffuse-Layer Effects on Time-Dependent Interfacial Kinetics" (Apr. 2004).
Borra, J.P., et al., Influence of electric Field Profile and Polarity on the Mode of EHDA Related to Electric Discharge Regimes J. of aerosol Science, 30(7) (1999) p. 913-925.
Brown, et al., "Pumping of Water with AC Electric Fields Applied to asymmetric Pairs of Microelectrodes" Physical review E, 63 (2000) p. 016305.
Chen, et al., "Dynamics of Inviscid Capillary Breakup: Collapse and Pinchoff of a Film Bridge" J. of Fluid Mechanics 341 (1997) p. 245-267.
Chiou, et al., "Light actuation of Liquid by Optoelectrowetting" Sensors and Actuators, 104 (2003) p. 222-228.
Chu, et al., "Electrochemical Thin Films at and Above the Classical Limiting Current".
Chun, et al., "The Electroviscous Force Between Charged Particles: Beyondthe Thin-Double-Layer approximation" Journal of Colloid and Interface Science, 274 (2004) p. 687-694.
Cloupeau, et al., "EHD Spraying Functioning Modes" (1032-1036).
Cohen, et al., "Shear-Induced Configurations of Confined Colloidal suspensions" Physical Review Letters, 93(4) (Jul. 2004) p. 046001-1-046001-4.
Deval, et al., "ADielectrophoretic Chaotic Mixer" (2002) p. 36-39.
Dinsmore, et al., "Colloidosomes: Selectively Permeable Capsules Composed of Colloidal Particles" Science 298 (Nov. 2002) p. 1006-1009.
Dukhin, S.S., "Non-equilibrium Electric Surface Phenomena" Advances in Colloid and Interface Science, 44 (1993) p. 1-134.
Eggers, Jens, "Universal Pinching of 3D axisymmetric Free-Surface Flow" Physical Review Letters, 71(21) (Nov. 1993) p. 3458-3460.
Eggleton, et al., "Tip Stream from a Drop in the Presence of Surfactants" Physical Review Letters, 87(4) (Jul. 2001) p. 048302.
Eloot, Sunny, "Experimental Evaluation of the Migration of Spherical Particles in Three-Dimensional Poiseuille Flow" Physics of Fluids, 16(7) (Jul. 2004) p. 2282-2293.
Feng, et al., "Interparticle Forces and Lift on a Particle Attached to a Solild Boundary in Suspension Flow" Physics of Fluids 14(1) (Jan. 2002) p. 49-60.
Fenn, et al., "Electrospray Ionization for Mass Spectrometry of Large Biomolecules" Science 246 (Oct. 1989) p. 64-71.
Gamero-Castano, et al., "Kinetics of Small Ion Evaporation from the Charge and Mass Distribution of Multiply Charged Clusters in Electrosprays" J. of Mass Spectrometry, 35 (2000) p. 790-803.
Gamero-Castano, et al., "Electric Measurements of Charged Sprays Emitted by Cone-Jets" J. fluid Mechanics, 459 (2002) p. 245-276.
Gamero-Castano, Manuel, "Electric-Field-Induced Ion Evaporation from Dielectric Liquid" Physical Review Letters 89(14) (Sep. 2002) p. 147602.
Gascoyne, et al., "Dielectrophoresis-Based Sample Handlinig in General-Purpose Programmable Diagnostic Instruments" Proceedings of the IEEE 92(1) (Jan. 2004) p. 22-42.
Gonzalez, et al., "fluid Flow Induced by Nonuniform AC Electric fields in Electrolytes on Microelectrodes. II. A Linear Double-Layer Analysis" Physical review E, 61(4) (Apr. 2000) p. 4019-4028.
Goranovic, Goran, "Electrohydrodynamic aspects of Two-fluid Microfluidic Systems: Theory and Simulation" Ph.D. Thesis (2003).
Grace, et al., "A Review of Liquid Atomizaiton by Electrical Means" J. of aerosol Sciencer, 25(6) (1994) p. 1005-1019.

Grahame, David, "The electrical Double Layer and the Theory of Electrocapillarity".
Green, et al., "Fluid Flow Induced by Nonuniform AC Electric Fields in Electrolytes on Microelectrodes. I. experimental Measurements" Physical Review E, 61(4) (Apr. 2000) p. 4011-4018.
Ijsebaert, et al., "Electro-Hydrodynamic Atomization of Drug solutions for Inhalation Purposes" J. of applied Physiology, 91 (2001) p. 2735-2741.
Jones, et al., "active Feedback-Controlled Dielectrophoretic Levitation" J. of applied Physiology 60(4) (Aug. 1986) p. 1247-1252.
Kaazoe, et al., "Measurements of electric Double Layer Between Electrolyte-Glass Interface by Evanescent Wave Light Illuminaiton".
Lapizco-Encinas, et al., "Insulator-Based Dielectrophoresis for the selective Concentration and Separation of Live Bacteria in Water" Electrophoresis, 25 (2004) p. 1695-1704.
Lastochkin, et al., "Electro-Kinetic Micro-Pump and Micro-Mixer Design on AC Faradaic Polarization" (2004).
Lauga, et al., "Evaporation-Driven Assembly of colloidal Particles" Physical Review Letters, 93 (2004) p. 238301.
Locke, Bruce, "Gas-Liquid Electrical Discharge Reactor Analysis" Proposal to the National Science Foundation (Jan. 2005).
Long, et al., "Electroosmotic flows Created by Surface Defects in Capillary Electrophoresis" J. of Colloid and Interface Science 212 (1999) p. 338-349.
Loscertales, et al., "Micro/Nano Encapsulation Via electrified coaxial Liquid jets" Science, 295 (Mar. 2002) p. 1695-1698.
Low, Peter, "Optimization of electrode Structures for DEP Microfluidic actuation: Application to Cantilever-Based Biological Sample Depositions" (Oct. 2003).
Luu, et al., "Characterization of an Electrospun Poly(Lactide-co-glycolide) and Block copolymer-Based Nanoostructured Matrix for DNA Delivery".
Meiners, et al., "Direct Measurement of Hydrodynamic Cross Correlations Between Two particles in an External Potential" Physical review Letters, 82(10) (Mar. 1999) p. 2211-2214.
Meinhart, et al., "Measurement of AC Electrokinetic Flows" J. of Biomedical Microdevices, 5(2) (2003) p. 141-147.
Merkel, et al., "electric fields in Fluidic Channels and Sensor applications with Capacitance" Sensors and Actuation, 80 (2000) p. 1-7.
Minerick, et al., "Manipulation and Characterization of Red Blood Cells with Alternating Current fields in Microdevices" Electrophoresis, (24) (2003) p. 3703-3717.
Mortensen, et al., "electro-Hydrodynamics of Bi-Ionic Electrolytes Driven by Modulated Surfaces" (2004).
Mpholo, et al., "Low Voltage Plug flow pumping Using Anisotropic electrode arrays" Sensors and Actuators, 92 (2003) p. 262-268.
Nadal, et al., "Eletrically Induced flows in the Vicinity of a dielectric stripe on a conducting plane" The European Physical Journal E, 9 (2002) p. 387-399.
Ogawa, Tomoya, "Measurement of the electrical conductivity and dielectric constant without contacting electrodes" J. of Applied Physics, 32(4) (1961) p. 583-592.
Okonski, Chester, "Electric properties of macromolecules. V. Theory of ionic polarization in polyelectrolytes" Theory of ionic Polarization in Plyelectrolytes (1960).
Ostubo, et al., "Dielectric Fluid Motors" applied Physics Letters, 71(3) (Jul. 1997) p. 318-320.
Papageorgiou, Demetrios, "On the Breakup of Viscous Liquid Threads" Phys. Fluids 7(7) (Jul. 1995) p. 1529-1544.
Pawlowski, et al., "Electrospun Electroactive Polymers for Aerospace Applications" American Institute of Aeronautics and Astronautics.
Ramos, et al., "AC Electrokinetics: A Review of Forces in Microelectrode Structures" J. Phys. D: Applied Physics, 31 (1998) p. 2338-2353.
Ramos, et al., "AC Electric-Field-Induced Fluid Flow in microelectrodes" Letter to the Editor, Journal of Colloid and Interface Science, 217 (1999) p. 420-422.
Radzihovsky, et al., "Novel Phases and Reentrant Melting of Two-Dimensional Colloidal Crystals" Physical Review E, 63 (2001) p. 031503.

Ramos, et al., "Pumping of Liquids with AC Voltages Applied to Asymmetric Pairs of Microelectrodes" Physical Review E, 67 (2003) p. 056302.

Rice, et al., "Electrokinetic Flow in a Narrow Cylindrical Capillary" The Journal of Physical Chemistry, 69 (11) (Nov. 1965) p. 4017-4024.

Sample, et al., "Production of Liquid Aerosols by Harmonic Electrical Spraying" Journal of Colloid and Interface Science, 41 (2) (Nov. 1972) p. 185-193.

Sato, Masayuki, "The Production of Essentially uniform-Sized Liquid Droplets in Gaseous or Immiscible Liquid Media Under Applied A.C. Potential" Journal of Electrostatics, 15 (1984) p. 237-247.

Secker, et al., "A Simple Liquid-Immersed Dielectric Motor" Journal of Applied Physics, 39 (6) (May 1968) p. 2957-2961.

Squires, et al., "Induced-Charge Electro-Osmosis" Journal of Fluid Mechanics, 509 (2004) p. 217-252.

Stoy, Richard, "Solution Procedure for the Laplace Equation in Bispherical Coordinates for Two Spheres in a Uniform External Field: Parallel Orientation" Journal of Applied Physics, 65 (7) (Apr. 1989) p. 2611-2615.

Stoy, Richard, "Solution Procedure for the Laplace Equation in Bispherical Coordinates for Two Spheres in a Uniform External Field: Perpendicular Orientation" Journal of Applied Physics, 66 (10) (Nov. 1989) p. 5093-5095.

Studer, et al., "Fabrication of Microfluidic Devices for AC Electrokinetic Fluid Pumping" Microelectronic Engineering, 61-62 (2002) p. 915-920.

Suehiro, et al., "Selective Detection of Viable Bacteria Using Dielectrophoretic Impedance Measurement Method" Journal of electrostatics, 57 (2003) p. 157-168.

Suehiro, et al., "High Sensitive Detection of Biological Cells Using Dielectrophoretic Impedance Measurement Method Combined with Electropermeabilizaiton" Sensors and Actuators B, 96 (2003) p. 144-151.

Suehiro, et al., "Selective Detection of Specific Bacteria Using Dielectrophoretic Impedance Measurement Method Combined with an Antigen-Antibody Reaction" Journal of Electrostatics, 58 (2003) p. 229-246.

Suzuki, et al., "Dielectrophoretic Micropatterning with Microparticle monolayers Covalently Linked to glass Surfaces" Langmuir, 20 (2004) p. 11005-11011.

Takhistov, et al., "Electrokinetic Displacement of Air Bubbles in Microchannels" Physics of fluids, 14 (Jan. 2002) p. 1-14.

Thorsen, et al., "Dynamic Pattern Formation in a Vesicle-Generating Microfluidic Device" Physical Review Letters, 86 (18) (Apr. 2001) p. 4163-4166.

Turner, James N., "AC Electrokinetic Tools for the Manipulation of Bioparticles" CNF Project #1197-04.

Ulander, et al., "Primary and Secondary Effective Charges for Electrical Double Layer systems with Asymmetric Electrolytes" Journal of Chemical Physics, 115 (15) (Oct. 2001) p. 7144-7160.

Veretennikov, et al., "Mechanism for Helical Gel Formation from Evaporation of Colloidal Solutions" Langmuir, 18 (2002) p. 8792-8798.

Wang, et al., "Dependence of Buffer Acidity and Ion Size on Electro-Osmotic mobility in Surfactant-Coated Silica Microchannels".

Wang, et al., "A Theoretical Method of Electrical Field Analysis for Dielectrophoretic electrode Arrays Using Green's Theorem" J. Phys. D: Applied Physics, 29 (1996) p. 1649-1660.

Wong, et al.. "Electrokinetics in Micro Devices for Biotechnology Applications" IEEE/ASME Transaction on Mechantronic (2003).

Yeo, et al., "A New AC Electrospray Mechanism by Maxwell-Wagner Polarization and Capillary Resonance" Physical Review Letters, 92 (13) (Apr. 2004) p. 133902.

Yuzhakov, et al., "Pattern Formation During Electropolishing" Physical Review B, 56 (19) (Nov. 1997) p. 12608-12624.

Zarraga, et al., "The Characterization of the Total Stress of Concentrated suspensions of Noncolloidal Spheres in Newtonian Fluids" Journal of Rheaology, 44 (2) (Mar./Apr. 2000) p. 185-220.

Zarraga, et al., "Normal Stress and Diffusion in a Dilute suspension of Hard Spheres Undergoing Simple Shear" Physics of Fluids, 13 (3) (Mar. 2001) p. 565-577.

Zarraga, et al., "Measurement of an Unexpectedly Large Shear-Induced Self-Diffusivity in a Dilute Suspension of Spheres" Physics of Fluids, 14 (7) (Jul. 2002) p. 2194-2201.

Gomez, Alessandro, "The electrospray and Its Application to Targeted Drug Inhalation" Abstract, Respiratory Care Journal 47 (12) (Dec. 2002).

* cited by examiner

FIG. 1

Prior Art

METHOD AND APPARATUS FOR AC ELECTROSPRAY

CROSS-REFERENCE TO RELATED APPLICATIONS

This application makes reference to and claims priority to U.S. Provisional Patent Application No. 60/511,365, entitled "High-Frequency AC Electro-sprays," filed Oct. 16, 2003, the entire contents and disclosure of which is hereby incorporated by reference.

BACKGROUND

1. Field of the Invention

The present invention relates generally to electrospray devices, and more particularly, to methods and apparatus for an alternating current (AC) electrospray operating in a vacuum or gaseous ambient medium with frequencies above 10 kHz.

2. Related Art

The application of a direct current (DC) electric field to generate charged liquid droplets from Taylor cones in DC electrospray is widely used in pharmaceutical mass-spectrometry because of its ability to produce a beam of relatively mono-dispersed and small (<100 nm) charged droplets that can contain individual protein molecules, see J. B. Fenn, M. Mann, C. K. Meng, S. F. Wong, and C. M. Whitehouse, Science 246, 64, 1989, the entire contents and disclosure of which is hereby incorporated by reference. Other areas of application include electrostatic printing, nano-particle technology, micro-encapsulation, fiber electrospinning, etc., see G. Castano, and V. Hruby, J. Fluid Mech. 459, 245, 2001, G. Loscertales, A. Barrero, I. Guerrero, R. Cortijo, M. Marquez, and A. M. Ganan-Calvo, Science 295, 1695, 2002, the entire contents and disclosures of which are hereby incorporated by reference. The DC field and interfacial charges combine to produce a Maxwell force that stretches the drop into a conic shape (known as a Taylor cone) and ejects streams of small charged droplets from the tip at large frequencies (>1 kHz).

The Taylor cone is formed due to a static balance between the azimuthal capillary stress and the Maxwell normal stress exerted by the predominantly tangential and singular electric field in the liquid. For electrolyte spraying from a DC Taylor cone, surface ions from the bulk electrolyte are transported and concentrated at the tip to drive a Rayleigh fission process. Spraying of dielectric liquid via DC Taylor cones is also possible, but it requires significantly higher voltages and is believed to be driven by the momentum and mass flux of an ion evaporation process at the cone tip, see M. Gamero-Castano and J. Fernandez de la Mora, J. of Mass Spectrom., 35, 790-803, 2000, the entire contents and disclosure of which is hereby incorporated by reference.

Figure 1:
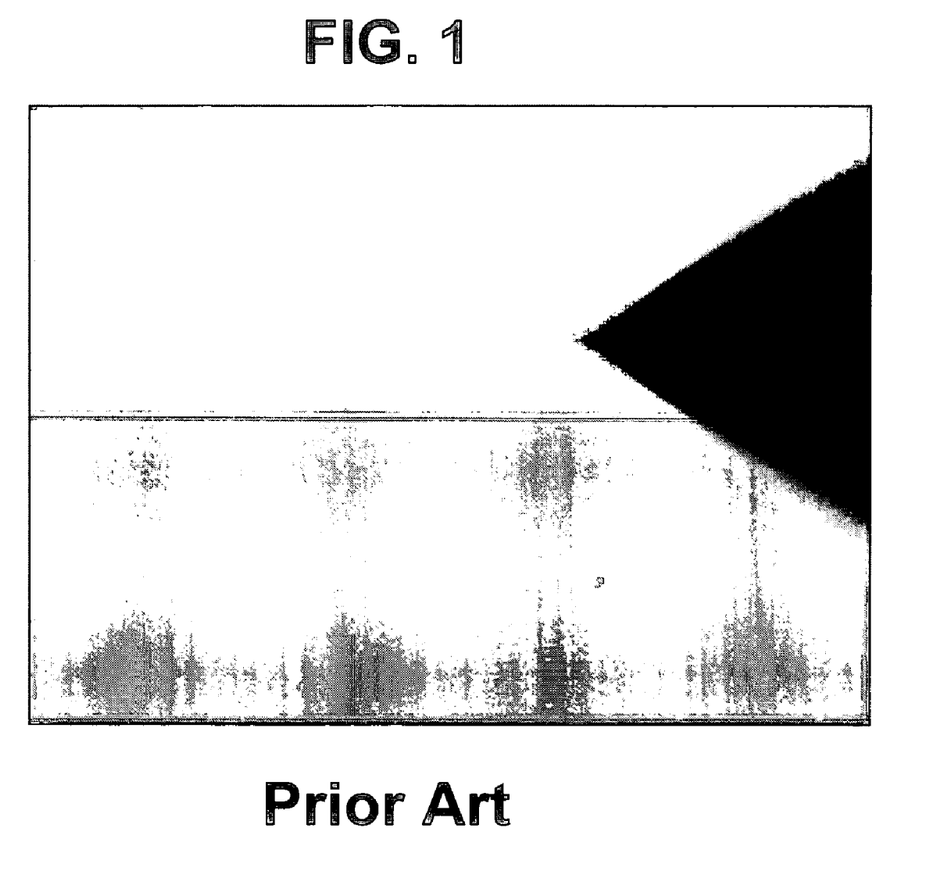
FIG. 1 is a depiction of the DC electrospray liquid meniscus which forms a steady Taylor cone. A jet emanates from the tip of the cone due to coulombic fission and subsequently breaks up to form a continuous stream of drops.
Figure 2:
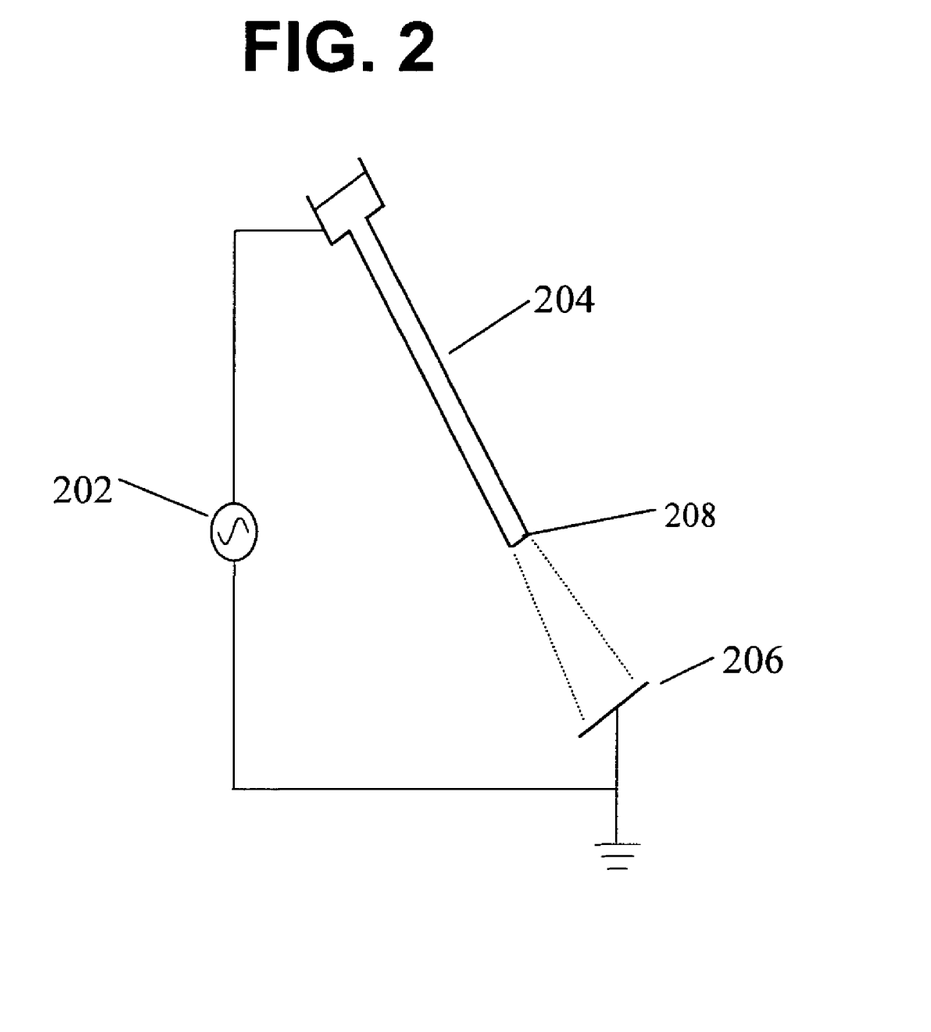
FIG. 2 is a schematic of an AC electrospray apparatus according to an embodiment of the present invention.
Figure 3A:
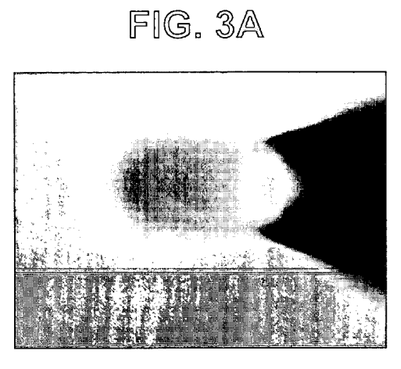
FIGS. 3A, 3B, 3C, and 3D show four consecutive images of AC electrospray of ethanol in air at a frequency of 70 kHz and a root mean squared voltage of 1750 V in accordance with an embodiment of the present invention. The frames are about 0.2 milliseconds apart and the captured event represents one drop ejection in a rapid sequence. Note that unlike the conic tips of DC and low-frequency AC sprays, the high-frequency AC electrospray has a rounded tip. Before ejection, the tip region elongates and expands as the neck shrinks until a micron-sized drop is ejected when the neck pinches.
Figure 3B:
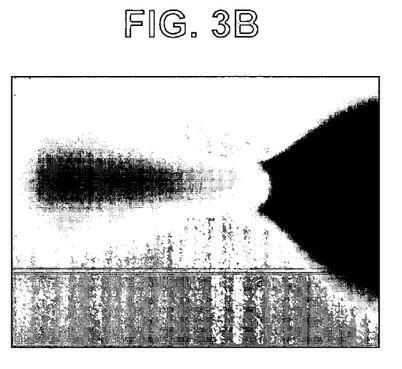
Figure 3C:
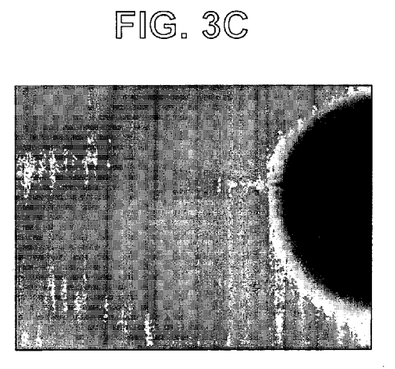
Figure 3D:
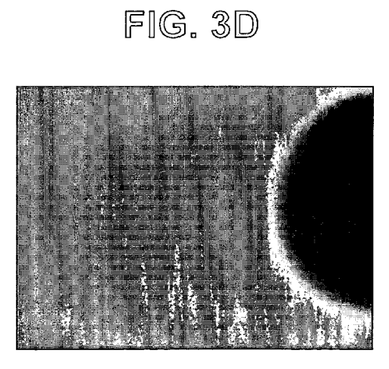
Figure 4:
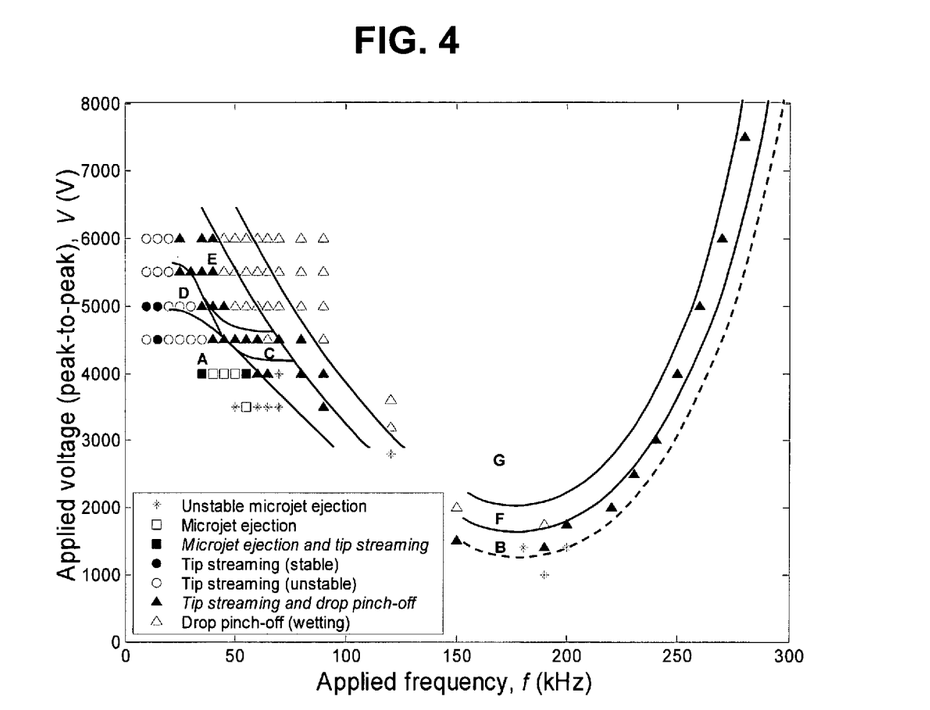
Figure 5:
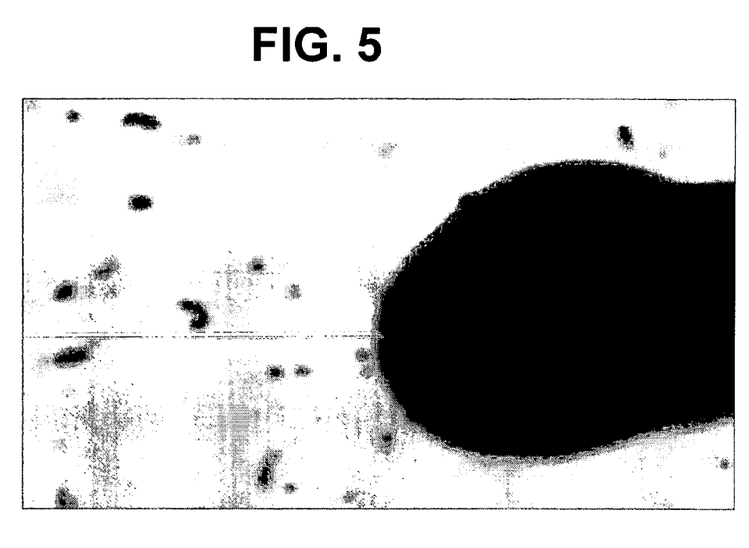
Figure 6:
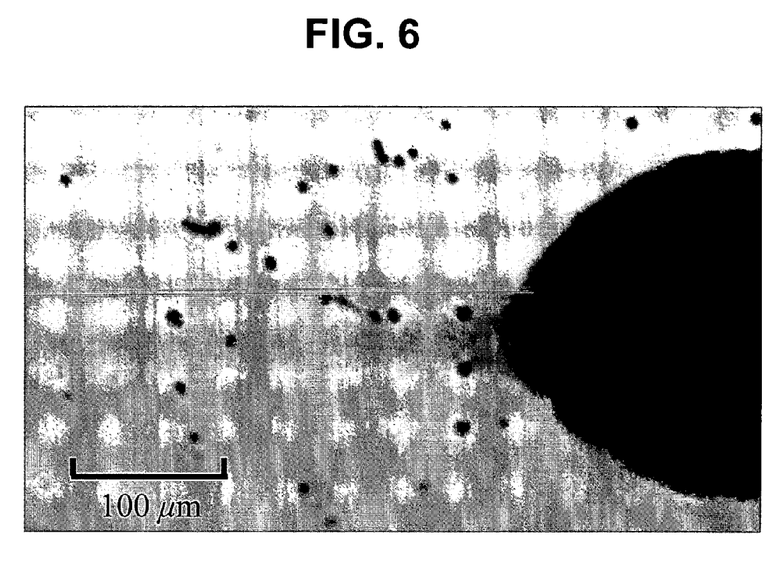
Figure 7:
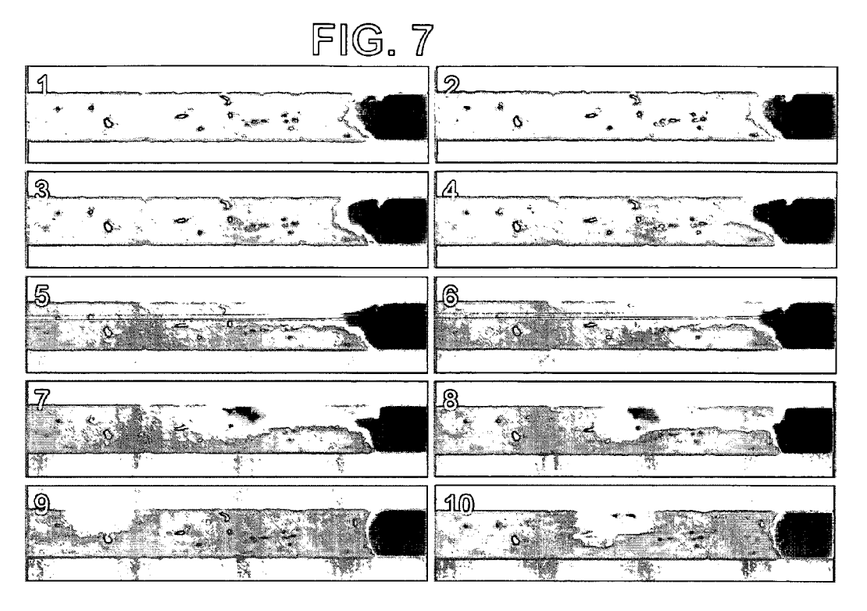

In DC electrospraying, a steady, continuous beam of sub-micron charged droplets (typically 0.2-0.3 microns) stream out in a Taylor cone. A typical image of a DC Taylor cone obtained by spraying ethanol into air using DC electric fields is shown in FIG. 1. The Taylor cone and the spray initiation for ethanol depends on several experimental conditions, but is typically observed beyond 2-3 kilovolts.

There has been little investigation into using an AC field for electrosprays. In earlier AC electrospray work it was expected that, at high frequency, the net Maxwell stress would vanish and drop ejection would be impossible. The few reported studies concentrated on low frequencies and superimposing a small AC bias onto a large DC field, see S. B. Sample, and R. Bollini, J. Colloid Interface Sci., 41, 185, 1972; and M. Sato, J. Electrostatics, 15, 237, 1984, the entire contents and disclosures of which are hereby incorporated by reference. Both of the studies described above, however, do not report spraying dynamics that are fundamentally different from DC electrosprays. One other reported work consisted of using a high frequency AC electric field with 30 kHz and 45 kHz frequencies, see G. Gneist and H. J. Bart, Chem. Eng. Technol., 25, 129-133, 2002, the entire contents and disclosure of which is hereby incorporated by reference. However, this work involved dispersing drops into an ambient liquid medium purely with the intention of generating emulsion drops in liquid/liquid systems.

SUMMARY

The present invention relates to an electrospray device using a high frequency alternating current above 10 kHz that provides a means for generating micron sized drops. The first broad aspect of the invention relates to the electrospray device. The second broad aspect of the invention relates to a method for producing liquid aerosol drops. The third broad aspect of the invention provides a method for microsphere encapsulation using biodegradable materials, whereas the last broad aspect of the invention provides a method of fiber synthesis using biodegradable materials.

According to the first broad aspect of the present invention, an electrospray device is provided comprising one or more micro-needles providing a passageway for transmission of a fluid; one or more conducting elements in electrical communication with the one or more micro-needles; and a source for generating an alternating current electric field with a frequency above 10 kHz across the one or more micro-needles and the one or more conducting elements.

According to the second broad aspect of the present invention, there is provided a method of producing liquid aerosol drops, the method comprising providing one or more micro-needles; introducing a fluid into the one or more micro-needles; providing one or more conducting elements in electrical communication with the one or more micro-needles; introducing an alternating current electric field with a frequency greater than approximately 10 kHz across the one or more micro-needles and the one or more conducting elements to induce the ejection of liquid aerosol drops from the one or more micro-needles.

According to the third broad aspect of the present invention, there is provided a method of microsphere encapsulation, comprising providing one or more micro-needles; introducing a fluid into the one or more micro-needles, wherein the fluid comprises a biodegradable material, a solvent and a material to be encapsulated; providing one or more conducting elements in electrical communication with the one or more micro-needles; and introducing an alternating current electric field with a frequency greater than approximately 10 kHz across the one or more micro-needles and the one or more conducting elements to induce the ejection of microspheres from the one or more micro-needles, wherein the microspheres contain the encapsulated material and the microspheres are encapsulated with the biodegradable material.

According to the fourth broad aspect of the present invention, there is provided a method of fiber synthesis, comprising providing one or more micro-needles; introducing a fluid into the one or more micro-needles, wherein the fluid comprises a biodegradable material and a solvent; providing one or more conducting elements in electrical communication with the one or more micro-needles; and introducing an alternating current electric field with a frequency greater than approximately 10 kHz across the one or more micro-needles and the one or more conducting elements to induce the ejection of fibers from the one or more micro-needles, wherein the fibers comprise the ejected biodegradable material.

BRIEF DESCRIPTION OF THE DRAWINGS

The invention will be described in conjunction with the accompanying drawings, in which:

FIG. 4 maps out various AC electrospray regimes in accordance with embodiments of the present invention suitable pumps or transmission mechanisms. The electric field acts to pull out a liquid meniscus at micro-needle tip 208 of micro-needle 204. Thus, according to an embodiment of the present invention, there is provided an electrospray device comprising one or more micro-needles providing a passageway for transmission of a fluid; one or more conducting elements in electrical communication with the one or more micro-needles; and a source for generating an alternating current electric field with a frequency above 10 kHz across the one or more micro-needles and the one or more conducting elements. A micro-needle of the present invention may be placed approximately 1 mm to approximately 25 mm away from the conducting elements. In operation, an electrospray device of the present invention may be placed in a vacuum or a gaseous ambient medium. Suitable ambient media include air, vacuum, trace gas, argon, helium, neon, etc. To accommodate the use of various ambient media, the entire electrospray apparatus may be housed in a sealed chamber connected to a vacuum pump or to inlet/outlet gas ports.

Suitable alternating current sources for use in embodiments of the present invention include all possible waveform signals such as sine waves, sawtooth waves, square waves, trapezoidal waves and triangle waves, amongst others.

Micro-needles of the present invention may be any suitable micro-needle now known or later developed including, metal hub micro-needles, metal hub syringe tip micro-needles, hypodermic stainless steel micro-needles, metallic spray heads, nozzles or tubes pierced with a hole, metallic conical tips, glass or plastic capillaries with electrode connections, etc. Micro-needles of the present invention may be exposed, insulated, or partially insulated. They may be mounted in various configurations, including horizontal, vertical, or any desired angle with respect to the horizontal plane. Micro-needles of the present invention may have channel diameters of between approximately 100 nm and approximately 1 cm.

Conducting elements of the present invention may be constructed of any suitable material such as a metallic (e.g., copper, brass, etc.) tape strip. A conducting element of the present invention may be a flat strip or a ring, or any other suitable shape.

According to an embodiment of the present invention, an alternating current electric field may be provided at a frequency of between approximately 10 kHz and approximately 10 MHz. According to an embodiment of the present invention, an alternating current electric field may be provided at a voltage of between approximately 100 V and 50,000 V. According to embodiments of the present invention, there are preferable operating window ranges between approximately 10 kHz and approximately 400 kHz and between approximately 500 V and approximately 5000 V. According to embodiments of the present invention, alternating current electric fields may be approximately greater than 500 V/cm.

In sharp contrast to the steady DC Taylor cone shown in FIG. 1, a conic geometry does not develop at the meniscus according to an embodiment of the present invention, as seen in FIGS. 3A, 3B, 3C, and 3D. Instead, the meniscus is pulled forward and a neck develops similarly to drops from a faucet. The drop beyond the neck elongates and expands considerably before the neck pinches off to eject the entire drop. Once the drop is ejected, the meniscus shrinks from its elongated state and the above cycle of events is repeated. The meniscus in AC electrosprays is thus observed to resonate whilst intermittently ejecting drops, in contrast to DC electrospraying in which the meniscus forms a steady Taylor cone from which drop ejection occurs in a continuous fashion. The AC electrospray behavior associated with the present invention, which is attributed to the interfacial polarization resulting from atmospheric ionization or interfacial liquid reaction, is not observed in the experiments of Gneist and Bart; their use of a liquid ambient medium suppresses the AC electrospray behavior that is provided by the present invention.

The entire pinch-off event lasts several milliseconds, much slower than the streaming pinch-off of DC sprays at the tip of the Taylor cone. The ejected drops are electro-neutral due to the large difference in the inverse AC frequency and the ejection time—the number of cations and anions, if they exist in the liquid, that have migrated into the drop due to the AC field should be roughly the same over the relatively long interval for drop pinch-off that contains hundreds or thousands of AC periods. The ejected drops, on the order of approximately 1 μm to approximately 10 μm in diameter, are also comparable or larger than the meniscus dimension and are much larger than the nm sized DC electrospray-created drops. Unlike DC drops, where coulombic fission that arises from charge repulsion within the drop leads to a relatively small size, AC electrospray-created drops may be larger because of their electro-neutrality.

Drops ejected in accordance with embodiments of the present invention may have diameters from approximately 1 nm to approximately 1000 μm.

The drop ejection window, characterized by the V-shaped curve in FIG. 4 is a strong function of the applied frequency. The critical onset voltage for drop ejection with typical solvents is approximately 0.5-1 kV, depending on the ambient medium used, compared to the higher critical onset voltage of 2-3 kV required for drop ejection in DC electrospraying.

In FIG. 4, the two boundaries of the drop ejection window and their separation both decrease with increasing applied frequency to a minimum at approximately 180 kHz before increasing again; drop ejection ceases entirely beyond approximately 400 kHz. Below the lower boundary of the voltage window, drops are not ejected as there is insufficient electrical stress to overcome the capillary stress in the micro-needle. The upper boundary is signified by a dramatic corona discharge that releases all charges from the meniscus such that it equilibrates into a spherical capillary shape, resulting in the cessation of further drop ejection. Also, at high frequencies and high voltages, an apparent electrowetting effect is observed that pushes liquid in the opposite direction up the micro-needle wall, thus suppressing further drop ejection, as depicted in FIG. 5.

In accordance with embodiments of the present invention, a meniscus is stable at low voltages and drops are ejected in a periodic manner. At the higher voltages of the operating window, the drops tend to eject in sequences with a long interval between ejection sequences. The meniscus oscillates between the ejection sequences at the capillary-viscous resonance frequency. At low applied frequencies, drop ejection occurs due to viscous pinch-off by a tip streaming mechanism, as illustrated in FIG. 6. As the applied frequency is increased beyond a frequency associated with the viscous-capillary pinch-off frequency of the drop, inertial effects dominate to pull out a long slender microjet, at the tip of which the drop detaches, as shown in FIG. 7.

Several experiments have been conducted with a number of liquids with different relative dielectric constants. Suitable liquids include dielectric liquids, electrolytes, methanol, ethanol, dichloromethane, acetone or mixtures thereof. The operating voltage window for methanol is lower than that of ethanol by a factor of 2 while there is an insignificant difference among the operating windows of ethanol, dichloromethane and acetone. An ethanol-water mixture of up to 50 percent by weight ethanol produces approximately the same voltage window as pure ethanol. Moreover, changing the ethanol electrolyte composition and conductivity by six orders of magnitude via addition of hydrochloric acid does not significantly change the voltage window or the ejection frequencies. Furthermore, when the water/dielectric liquid volume ratio exceeds about one, the spraying ceases, or at least diminishes to an insignificant amount. This may be attributed to the high ionization potential of water, which does not allow a gas phase ionization reaction to occur. Low volatility of the aqueous solution and high surface tension may also play a role.

Figure 8:
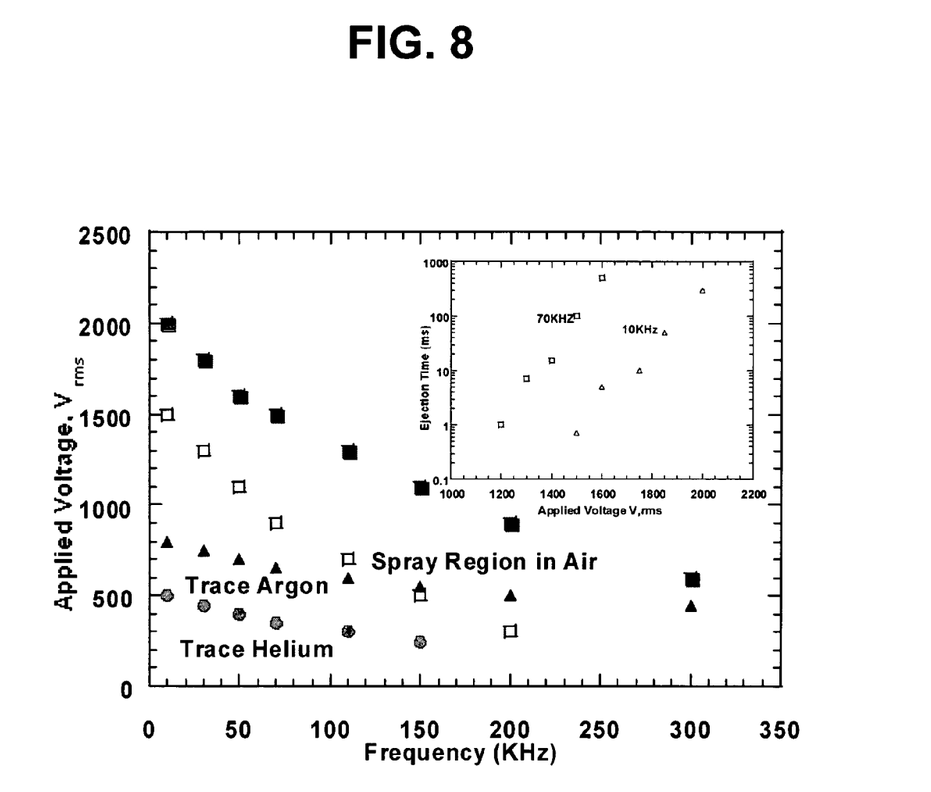

As depicted in FIG. 8, the drop ejection window is shifted downward thereby lowering the critical onset voltage for drop ejection when air is replaced by inert gases such as argon, helium or neon as the ambient medium. These gases catalyze the ionization of gas which, in turn, results in greater polarization at the meniscus interface for a given voltage, thus enabling drops to be pulled out from the meniscus and pinched-off with greater force.

The production of micron-sized electro-neutral drops using embodiments of the present invention provides a design for a portable respiratory drug delivery device that may be administered directly by electrospraying of drug compounds such as asthmatic steroids (beclomethasone dipropionate), insulin or exogenous lung surfactant (Surfactant Replacement Therapy) to treat asthmatic and diabetic patients, and, neonates suffering from Respiratory Distress Syndrome (RDS). When conventional inhalation devices are used, only small fractions of the drug reach the lower airways; most of the drug is deposited in the mouth or throat, and subsequently absorbed in the gastrointestinal tract. Direct local administration to target organs such as a lung provides an immediate effect, thus requiring lower drug quantities compared to oral delivery.

The present invention has several advantages over DC electrosprays. The electro-neutral drops of the present invention do not have to be neutralized before administration to the patient. Moreover, prior research has indicated that uniform distributions of droplets 2.8 µm in size results in optimum dose efficiency, see J. C. Ijsebaert, K. B. Geerse, J. C. M. Marijnissen, J. W. J. Lammers and P. Zanen, J. Appl. Physiol., 91, 2735, 2001; and A. Gomez, Resp. Care, 47, 1419, 2002, the entire contents and disclosures of which are hereby incorporated by reference. The micron-sized drops obtained using the AC electrosprays in accordance with the present invention therefore present a distinct advantage to the nanodrops obtained using DC electrosprays. One other distinct advantage of the electro-neutral drops obtained using AC electrospraying in accordance with the present invention is that the low power requirement reduces power consumption, increases safety, and presents potential for the device to be miniaturized to dimensions commensurate with portability.

Thus, according to an embodiment of the present invention, there is provided a method of producing liquid aerosol drops, the method comprising providing one or more micro-needles; introducing a fluid into the one or more micro-needles; providing one or more conducting elements in electrical communication with the one or more micro-needles; introducing an alternating current electric field with a frequency greater than approximately 10 kHz across the one or more micro-needles and the one or more conducting elements to induce the ejection of liquid aerosol drops from the one or more micro-needles.

The present invention may also be used as a microencapsulation technique to encapsulate drugs, DNA, proteins, osteogenic or dermatological growth factors, bacteria, viruses, fluorescent particles and immobilized enzyme receptors for controlled release drug delivery, bone or tissue engineering, storage of positive controls in clinical or environmental field tests or biosensors for clinical diagnostics and environmental, water or illicit drug monitoring.

A microencapsulation technique of the present invention involves spraying a microemulsion consisting of a material to be encapsulated dissolved in water within a continuous phase of organic solvent (e.g., dichloromethane, a dichloromethane/ethanol mixture, a dichloromethane/butanol mixture, etc.) in which a biocompatible and biodegradable polymeric excipient (e.g., poly-glycolic-acid, poly-lactic-acid, poly-L-lactic-acid and poly-lactic-acid-glycolic-acid) is dissolved. The solvent evaporates as the spray drops release into the atmosphere, leaving a polymer shell in which the drug is encapsulated.

Thus, according to an embodiment of the present invention, there is provided a method of microsphere encapsulation, comprising providing one or more micro-needles; introducing a fluid into the one or more micro-needles, wherein the fluid comprises a biodegradable material, a solvent and a material to be encapsulated; providing one or more conducting elements in electrical communication with the one or more micro-needles; and introducing an alternating current electric field with a frequency greater than approximately 10 kHz across the one or more micro-needles and the one or more conducting elements to induce the ejection of microspheres from the one or more micro-needles, wherein the microspheres contain the encapsulated material and the microspheres are encapsulated with the biodegradable material.

Figure 9A:
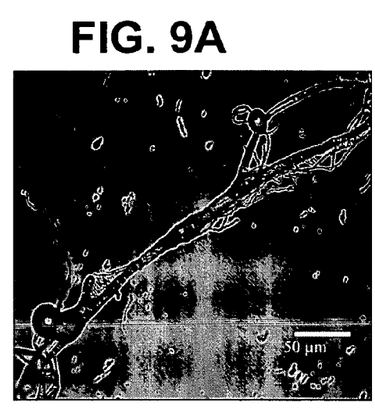
Figure 9B:
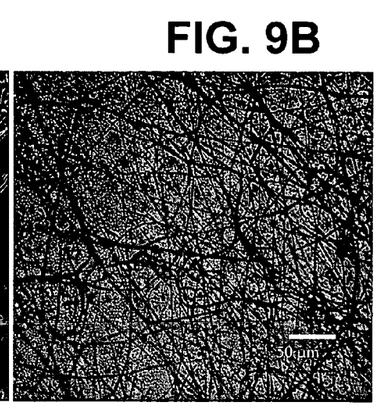

A similar technique used for microencapsulation may be used to synthesize bio-fibers for tissue and bone engineering. Composite fibers with diameters between approximately 100 nm and approximately 100 µm, as shown in FIG. 9A, or a mesh network of single strand fibers with diameters between approximately 1 nm and approximately 100 µm with adjustable pore sizes between approximately 10 nm and approximately 1 cm, as shown in FIG. 9B, may be produced. These may be used as surgical threads, medical gauze or bioscaffolds for bone or tissue engineering.

The synthesis of fibers described above with the microencapsulation techniques of the present invention allows the encapsulation of dermatological or osteogenic growth factors for bone or tissue engineering as well as antibodies or coloring agents for clothing to be encapsulated within the fiber.

Thus, according to an embodiment of the present invention, there is provided a method of fiber synthesis comprising providing one or more micro-needles; introducing a fluid into the one or more micro-needles, wherein the fluid comprises a biodegradable material and a solvent; providing one or more conducting elements in electrical communication with the one or more micro-needles; and introducing an alternating current electric field with a frequency greater than approximately 10 kHz across the one or more micro-needles and the one or more conducting elements to induce the ejection of fibers from the one or more micro-needles, wherein the fibers comprise the ejected biodegradable material.

All documents, patents, journal articles and other materials cited in the present application are hereby incorporated by reference. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An electrospray device comprising:
   one or more micro-needles providing a passageway for transmission of a fluid, each of said micro-needles having a micro-needle tip;
   one or more conducting elements in electrical communication with said one or more micro-needles; and
   a source for generating an alternating current electric field with a frequency above 10 kHz across said one or more micro-needles and said one or more conducting elements, wherein the electric field pulls out a liquid meniscus at each micro-needle tip to thereby form liquid aerosol drops from said one or more micro-needles.

2. The electrospray device of claim 1, further comprising an external pump connected to said one or more micro-needles, wherein, when in operation, the fluid flows through said one or more micro-needles by a pressure-gradient imposed by said external pump.

3. The electrospray device of claim 1, wherein said one or more micro-needles has a channel diameter of between approximately 100 nm and approximately 1 cm.

4. The electrospray device of claim 1, wherein said one or more micro-needles comprises a metal hub syringe.

5. The electrospray device of claim 1, wherein said one or more micro-needles comprises a metal hub syringe tip.

6. The electrospray device of claim 1, wherein said one or more micro-needles is exposed.

7. The electrospray device of claim 1, wherein said one or more micro-needles is insulated.

8. The electrospray device of claim 1, wherein said one or more micro-needles is partially insulated.

9. The electrospray device of claim 1, wherein said one or more micro-needles is mounted horizontally, vertically, or at any angle with respect to the horizontal plane.

10. The electrospray device of claim 1, wherein said one or more conducting elements is located between approximately 1 mm and approximately 25 mm from each said micro-needle tip.

11. The electrospray device of claim 1, wherein said one or more conducting elements comprises a flat strip or a ring.

12. The electrospray device of claim 1, wherein said alternating current electric field source is capable of operating at frequencies between 10 kHz and 10 MHz.

13. The electrospray device of claim 1, wherein said alternating current electric field is capable of operating at voltages between 100 V and 50,000 V.

14. A method of producing liquid aerosol drops, said method comprising:
   providing one or more micro-needles;
   introducing a fluid into said one or more micro-needles;
   providing one or more conducting elements in electrical communication with said one or more micro-needles;
   introducing an alternating current electric field with a frequency greater than approximately 10 kHz across said one or more micro-needles and said one or more conducting elements to induce the ejection of liquid aerosol drops from said one or more micro-needles.

15. The method of claim 14, wherein said liquid aerosol drops are electro-neutral.

16. The method of claim 14, wherein said liquid aerosol drops are between approximately 1 nm and approximately 1000 μm in diameter.

17. The method of claim 14, wherein said fluid comprises a dielectric liquid or a mixture of dielectric liquids.

18. The method of claim 17, wherein said dielectric liquid comprises methanol.

19. The method of claim 17, wherein said dielectric liquid comprises ethanol.

20. The method of claim 17, wherein said dielectric liquid comprises ethanol and water.

21. The method of claim 17, wherein said dielectric liquid comprises dichloromethane.

22. The method of claim 17, wherein said dielectric liquid comprises acetone.

23. The method of claim 14, wherein said fluid comprises an electrolyte or a mixture of electrolytes.

24. The method of claim 14, wherein said fluid comprises a mixture of dielectric liquids and electrolytes.

25. The method of claim 14, wherein said fluid comprises a drug.

26. The method of claim 14, wherein said fluid comprises an asthmatic steroid.

27. The method of claim 14, wherein said fluid comprises insulin.

28. The method of claim 14, wherein said fluid comprises an exogenous lung surfactant.

29. The method of claim 14, wherein said method is conducted in a vacuum or a gaseous ambient medium.

30. The method of claim 29, wherein said ambient medium of operation comprises air.

31. The method of claim 29, wherein said ambient medium of operation comprises a vacuum.

32. The method of claim 29, wherein said ambient medium of operation comprises a trace gas.

33. The method of claim 29, wherein said ambient medium of operation comprises argon.

34. The method of claim 29, wherein said ambient medium of operation comprises helium.

35. The method of claim 29, wherein said ambient medium of operation comprises neon.

36. The method of claim 14, wherein said alternating current electric field is at a frequency of between approximately 10 kHz and approximately 10 MHz.

37. The method of claim 14, wherein said alternating current electric field is at a voltage of between approximately 100 V and approximately 25,000 V.

38. The method of claim 14, wherein each of said one or more micro-needles comprises a tip and said one or more conducting elements is placed between approximately 1 mm and approximately 25 mm from each said micro-needle tip.

39. The method of claim 14, wherein said fluid is moved through said one or more micro-needles by operation of gravity.

40. The method of claim 14, wherein said fluid is moved through said one or more micro-needles by operation of an external pump connected to said one or more micro-needles.

41. The method of claim 14, wherein said liquid aerosol drops are ejected intermittently.

* * * * *